United States Patent
Knaup et al.

(10) Patent No.: US 11,441,119 B2
(45) Date of Patent: Sep. 13, 2022

(54) CULTURE MEDIA COMPRISING N-ACYL-X-GLUTAMINE DIPEPTIDES

(71) Applicant: Evonik Operations GmbH, Essen (DE)

(72) Inventors: Guenter Knaup, Bruchkoebel (DE); Friedhelm Merz, Nierstein (DE)

(73) Assignee: Evonik Operations GmbH, Essen (DE)

( * ) Notice: Subject to any disclaimer, the term of this patent is extended or adjusted under 35 U.S.C. 154(b) by 461 days.

(21) Appl. No.: 16/490,811

(22) PCT Filed: Mar. 2, 2018

(86) PCT No.: PCT/EP2018/055192
§ 371 (c)(1),
(2) Date: Sep. 3, 2019

(87) PCT Pub. No.: WO2018/162352
PCT Pub. Date: Sep. 13, 2018

(65) Prior Publication Data
US 2020/0024571 A1    Jan. 23, 2020

(30) Foreign Application Priority Data
Mar. 9, 2017    (EP) .................... 17160020

(51) Int. Cl.
*C12N 5/00* (2006.01)
*C12N 5/071* (2010.01)

(52) U.S. Cl.
CPC ......... *C12N 5/0037* (2013.01); *C12N 5/0682* (2013.01); *C12N 2500/30* (2013.01); *C12N 2500/32* (2013.01); *C12N 2500/90* (2013.01)

(58) Field of Classification Search
CPC ............ C12N 5/0037; C12N 5/0682; C12N 2500/32; C12N 2500/90
See application file for complete search history.

(56) References Cited

U.S. PATENT DOCUMENTS

| 5,534,538 A | * | 7/1996 | Drauz | C07K 5/06026 514/21.91 |
| 5,543,397 A | | 8/1996 | Drauz et al. | |
| 5,786,337 A | * | 7/1998 | Frenzel | A01N 1/02 435/1.1 |
| 2003/0134851 A1 | | 7/2003 | Baxter et al. | |

OTHER PUBLICATIONS

Sánchez-Kopper et al., Tracking dipeptide at work-uptake and intracellular fate in CHO culture. AMB Express, vol. 6 (2016) article 48. (Year: 2016).*
International Search Report and Written Opinion dated May 14, 2018 in PCT/EP2018/055192 filed on Mar. 2, 2018.
European Search Report dated Apr. 19, 2017 in European Patent Application No. 17 16 0020 filed on Mar. 9, 2017.
Sánchez-Kopper, A. et al., "Tracking dipeptides at work-uptake and intracellular fate in CHO culture", AMB Express, vol. 6, No. 1, 2016, XP055365341, pp. 1-12.
Kim, D. Y. et al., "Fed-Batch CHO Cell t-PA Production and Feed Glutamine Replacement to Reduce Ammonia Production", Biotechnology Progress, vol. 29, No. 1, 2013, XP009191145, pp. 165-175.
Imamoto, Y. et al., "Advantages of AlaGln as an additive to cell culture medium: use with anti-CD20 chimeric antibody-producing Potelligent™ CHO cell lines", Cytotechnology, vol. 65, No. 1, 2013, XP035159425, pp. 135-143.
Van Der Valk, J. et al., "Optimization of chemically defined cell culture media—Replacing fetal bovine serum in mammalian in vitro methods", Toxicology in Vitro, vol. 24, No. 4, 2010, XP027048454, pp. 1053-1063.
Salazar, A. et al., "Amino acids in the cultivation of mammalian cells", Amino Acids, vol. 48, No. 5, 2016, XP035889636, pp. 1161-1171.

* cited by examiner

*Primary Examiner* — Kara D Johnson
(74) *Attorney, Agent, or Firm* — Oblon, McClelland, Maier & Neustadt, L.L.P.

(57) ABSTRACT

Disclosed herein is a cell culture media containing L-glutamine from a set of N-acylated dipeptides Acyl-X-Q, and L-glutamine from a set of other glutamine-sources Qsource in a defined molar ratio $R=n(Acyl-X-Q)/n(Qsource)$, wherein the variables X, Q, Acyl, R, $n(Acyl-X-Q)$ and $n(Qsource)$ are defined in the general disclosure. Processes of using the cell culture media are also described herein.

13 Claims, No Drawings

US 11,441,119 B2

CULTURE MEDIA COMPRISING N-ACYL-X-GLUTAMINE DIPEPTIDES

FIELD OF THE INVENTION

The present invention relates to biotechnological production processes. More specifically, the present invention relates to improved culture media for use in biotechnological production processes, processes employing such improved media, and to products obtained from the processes using the improved culture media.

BACKGROUND OF THE INVENTION

Biotechnological processes are widely used for the production of biological products. These processes typically involve the cultivation of cells in a culture medium under conditions permissible to the growth and product formation by the cultivated cells. Cells useful in biotechnological production are bacterial cells, fungal cells, yeast cells, and cells of animal or plant origin. Animal cell culture has long been used for the production of biological products, such as therapeutic proteins, polypeptides, peptides or other biological molecules, such as therapeutic polysaccharides. In such cell culture processes, animal cells, normally genetically modified to produce a desired product, are cultivated in a liquid, solid or semi solid culture medium for cell proliferation and product formation. One significant advantage of cell culture is the fact that animal cells and plant cells are able to perform post-translational modifications of the primary product, such as folding and post-translational modification of a polypeptide.

In biotechnological production processes, in particular in animal cell cultures, control and optimization of the cell culture conditions is critical for cell proliferation and product formation. One decisive factor is medium composition. The concentration and quality of the final cell culture product depends heavily on the medium composition. Animal and plant cell cultures are particularly demanding in terms of the required nutrient composition and culture conditions. Required nutrients not only include basic sources for carbon, nitrogen and energy, such as sugar and ammonia, but also more complex nutrients, such as essential amino acids, and vitamins may be required. For this reason, supplementation of animal cell culture media with complex nutrient compositions, such as serum, has been used to provide the animal cells with a broad variety of nutrients. However, regulatory and safety concerns, as well as problems with the heterogeneity of the available sources of sera has led the industry to strive towards eliminating serum and other non-defined media from industrial cell culture processes. Cell cultures grown in serum-free media, however, often show nutritional deficiencies. For this reason, much effort has been given to identify those nutritional components of complex media, as well as their optimal concentrations, which are required for satisfactory growth and protein formation in cell cultures.

The supply of cell cultures with amino acids is known to have a significant effect on growth rate and production. Glutamine is routinely used in cell culture media, since it is an important source of carbon, nitrogen and energy for the cultured cells. It was demonstrated that the amount of glutamine necessary for optimal growth of animal cell cultures is 3 to 10 times greater than the amount of other amino acids (Eagle et al., Science 130:432-37). However, glutamine as a nutrient is unstable when dissolved in water at elevated temperatures, such as heat sterilizing conditions, because pyroglutamate and ammonia are formed under heat (Roth et al. 1988, In Vitro Cellular & Developmental Biology 24(7): 696-98). For this reason, glutamate is often used in cell culture media instead of glutamine (Cell Culture Technology for Pharmaceutical and Cell-based Therapies, 52, Sadettin et al., Eds., Taylor and Francis Group, 2006). Other groups have tried to avoid the formation of unwanted substances, such as pyroglutamate and ammonia, by adding glutamine-containing dipeptides, such as alanyl-glutamine or glycyl-glutamine, to the cell culture medium (Roth et al. (1988), In Vitro Cellular & Developmental Biology 24(7): 696-98). Yet other groups have proposed acylating dipeptides in order to make them more stable under heat sterilization conditions. U.S. Pat. No. 5,534,538 describes N-acyl dipeptides and their use in heat sterilized enteral or parenteral nutrition products.

EP 0220379 and DE3538310 disclose the use of glutamine-containing dipeptides and tripeptides in cell culture media. Glutamine is added in form of dipeptides, in order to avoid problems stemming from the instability of glutamine under elevated temperatures. The glutamine-containing dipeptides are used as a temperature insensitive glutamine source.

JP61271985 discloses a culture medium useful for animal cells including the dipeptides Xxx-L-glutamine, wherein Xxx is glycine, D/L-alanine, L-aspartic acid, L-glutamic acid, L-valine, L-leucine, L-serine, L-lysine or L-phenylalanine.

While cell culture media described in the prior art provide satisfactory performance and properties for certain cell culture processes, there is still a need for cell culture media promoting improved product formation in biotechnological production processes.

THE PRESENT INVENTION

In the context of the present invention, it was found that the following cell culture media increase the productivity of biotechnological production processes:

Cell culture media comprising L-glutamine from a set of N-acylated dipeptides Acyl-X-Q and L-glutamine from a set of other glutamine-sources Qsource in a defined molar ratio $R=n(Acyl-X-Q)/n(Qsource)$;

wherein X is defined as an L-amino acid;

wherein Q is defined as L-glutamine attached via an amide bond to L-amino acid X;

wherein Acyl is defined as a $C_1$-$C_7$-acyl moiety attached via an amide bond to the amino-terminus of L-amino acid X;

wherein R is defined to be in the range of 0,03 to 20;

wherein n(Acyl-X-Q) is the total amount of substance of L-glutamine contained in the set of N-acylated dipeptides Acyl-X-Q in the culture media; and wherein n(Qsource) is the total amount of substance of L-glutamine contained in the set of other glutamine sources Qsource in the culture media.

The constituents of the set of other L-glutamine sources Qsource are selected from the following: free L-glutamine, dipeptides Y-Q, or mixtures thereof, wherein Y is defined as one of the 20 genetically encoded L-amino acids, wherein Q is defined as L-glutamine attached via an amide bond to L-amino acid Y, wherein the amide bond connecting Y and Q in dipeptide Y-Q is a regular backbone amide bond involving the carboxy terminus of amino acid Y and the amino terminus of glutamine Q.

In a first aspect the present invention relates to above disclosed culture media. The present invention, further, relates to the use of such cell culture media for culturing cells as well as to processes for the manufacture of cell culture products, comprising the step: Contacting cells with a cell culture medium as disclosed herein.

DETAILED DESCRIPTION OF THE INVENTION

A "culture medium", according to the invention, shall be understood as being a liquid or solid medium containing nutrients, the medium being suitable for nourishing and supporting life and/or product formation of cells in the culture. The cultured cells, according to the invention, may be bacterial cells, yeast cells, fungal cells, animal cells, such as mammalian cells or insect cells, and/or plant cells, e.g., algae. Typically, a culture medium provides essential and non-essential amino acids, vitamins, at least one energy source, lipids, and trace elements, all required by the cell for sustaining life, growth and/or product formation. The culture medium may also contain components that enhance growth and/or survival above the minimal rate, including hormones and growth factors. The culture medium has preferably a pH and a salt concentration which supports life, growth and/or product formation of the cells. A culture medium, according to the invention, preferably comprises all nutrients necessary to sustain life and proliferation of the cell culture. Preferred culture media are defined media.

A "chemically defined medium", according to the invention is a medium that contains no cell extracts, cell hydrolysates, or protein hydrolysates. Chemically defined media comprise no components of unknown composition. As is commonly understood by the person skilled in the art, chemically defined media are usually free of animal-derived components. All components of a chemically defined medium have a known chemical structure. Culture media other than defined culture media may be referred to as "complex" culture media.

A "cell culture medium" shall be understood as being a culture medium suitable for sustaining life, proliferation and/or product formation of animal cells and/or plant cells.

A "nutrient", according to the present invention, is a chemical compound or substance which is needed by cells to live and grow. The nutrient is preferably taken up by the cell from the environment. Nutrients can be "organic nutrients" and "inorganic nutrients". Organic nutrients include carbohydrates, fats, proteins (or their building blocks, e.g., amino acids), and vitamins. Inorganic nutrients are inorganic compounds such as, e.g., dietary minerals and trace elements. "Essential nutrients" are nutrients which the cell cannot synthesize itself, and which must thus be provided to the cell by the culture medium.

A "cell culture product", according to the invention, shall be understood as being any useful biological compound produced by cells in cell culture. Preferred cell culture products of the invention are therapeutic proteins, diagnostic proteins, therapeutic polysaccharides, such as heparin, antibodies, e.g., monoclonal antibodies, growth factors, interleukin, peptide hormones, and enzymes.

A "free amino acid", according to the invention, is understood as being an amino acid having its amino and its (alpha-) carboxylic functional group in free form, i.e., not covalently bound to other molecules, e.g., an amino acid not forming a peptide bond. Free amino acids may also be present as salts or in hydrate form. When referring to an amino acid as a part of, or in, a peptide, this shall be understood as referring to that part of the respective peptide structure derived from the respective amino acid.

A "growth factor", according to the invention, shall be understood as being any naturally occurring substance capable of stimulating cellular growth, proliferation and cellular differentiation. Preferred growth factors are in form of protein or steroid hormone. According to one embodiment of the invention, the expression "growth factor" shall be interpreted as relating to a growth factor selected from the list consisting of fibroblast growth factor (FGF), including acidic FGF and basic FGF, insulin, insulin-like growth factor (IGF), epithelial growth factor (EGF), nerve growth factor (NGF), platelet-derived growth factor (PDGF), and transforming growth factor (TGF), including TGFalpha and TGFbeta, cytokine, such as interleukins 1, 2, 6, granulocyte stimulating factor, and leukocyte inhibitory factor (LIF).

A "peptide" according to the invention, shall be understood as being a peptide compound consisting of 2 to 20 amino acids.

The expression "N-acylated", with reference to an amino acid, shall be understood as meaning that the N-acylated amino acid is modified by the addition of an acyl group to the alpha-amino group of the amino acid.

A "sterile form" of a nutrient composition, culture medium, cell culture medium, or the like, shall be understood as defining the absence of any living matter in said composition, culture medium, cell culture medium or the like.

A "solid culture medium", in the context of the present invention, shall be understood as being any non-liquid or non-gaseous culture medium. Preferred solid culture media of the invention are gel-like culture media, such as agar-agar, carrageen or gelatine.

"Passaging of cells" (also known as subculture or splitting of cells), in the context of the present invention, is understood as meaning the transferring a small number of cells into a new culture vessel. Cells can be cultured for a longer time if they are split regularly, as it avoids the senescence associated with prolonged high cell density. Suspension cultures are easily passaged with a small amount of culture containing a few cells diluted in a larger volume of fresh media.

The present invention relates to cell culture media comprising L-glutamine from a set of N-acylated dipeptides Acyl-X-Q and L-glutamine from a set of other glutamine-sources Qsource in a defined
  molar ratio R=n(Acyl-X-Q)/n(Qsource);
  wherein X is defined as an L-amino acid;
  wherein Q is defined as L-glutamine attached via an amide bond to L-amino acid X;
  wherein Acyl is defined as a $C_1$-$C_7$-acyl moiety attached via an amide bond to the amino-terminus of L-amino acid X;
  wherein R is defined to be in the range of 0,03 to 20;
  wherein n(Acyl-X-Q) is the total amount of substance of L-glutamine contained in the set of N-acylated dipeptides Acyl-X-Q in the culture media; and
  wherein n(Qsource) is the total amount of substance of L-glutamine contained in the set of other glutamine sources Qsource in the culture media.

The constituents of the set of other L-glutamine sources Qsource are selected from the following: free L-glutamine, dipeptides Y-Q, or mixtures thereof, wherein Y is defined as one of the 20 genetically encoded L-amino acids, wherein Q is defined as L-glutamine attached via an amide bond to L-amino acid Y, wherein the amide bond connecting Y and Q in dipeptide Y-Q is a regular backbone amide bond involving the carboxy terminus of amino acid Y and the amino terminus of glutamine Q.

In preferred embodiments of the present invention the constituents of the set of other L-glutamine sources Qsource are selected from the following: free L-glutamine, dipeptide Y-Q, wherein Y is Alanine, or mixtures thereof. In further preferred embodiments of the present invention the only constituent of the set of other L-glutamine sources Qsource is dipeptide Y-Q, wherein Y is Alanine.

The present inventors found that cell culture media of this kind have superior properties over prior art cell culture media. It was found by the present inventors that providing sources of L-glutamine in the ratio as specified results in increased productivity of cell cultures.

According to the present invention L-amino acid X in the N-acylated dipeptide Acyl-X-Q can be any natural L-amino acid, i.e. any of the 20 genetically encoded L-amino acids, i.e. X is selected from the following:

| | |
|---|---|
| Alanine | (Ala/A) |
| Arginine | (Arg/R) |
| Asparagine | (Asn/N) |
| Aspartic acid | (Asp/D) |
| Cysteine | (Cys/C) |
| Glutamic acid | (Glu/E) |
| Glutamine | (Gln/Q) |
| Glycine | (Gly/G) |
| Histidine | (His/H) |
| Isoleucine | (Ile/I) |
| Leucine | (Leu/L) |
| Lysine | (Lys/K) |
| Methionine | (Met/M) |
| Phenylalanine | (Phe/F) |
| Proline | (Pro/P) |
| Serine | (Ser/S) |
| Threonine | (Thr/T) |
| Tryptophan | (Trp/W) |
| Tyrosine | (Tyr/Y) |
| Valine | (Val/V). |

In a preferred embodiment of the present invention, X is selected from the 20 genetically encoded L-amino acids with the exception of glutamine.

In other preferred embodiments of the present invention, X is selected from: Ala, Gly, Asn. In further preferred embodiments of the present invention X is Ala.

According to the present invention the amide bond connecting X and Q in the N-acylated dipeptide Acyl-X-Q is a regular backbone amide bond involving the carboxy terminus of amino acid X and the amino terminus of glutamine Q.

According to the present invention the $C_1$-$C_7$-acyl moiety of N-acylated dipeptides Acyl-X-Q is defined as acyl group $R^4$—C(O)—, wherein $R^4$ is linear or branched $C_1$-$C_6$-alkyl or $C_3$-$C_6$-cycloalkyl.

Useful linear or branched chain $C_1$-$C_6$-alkyl groups include methyl, ethyl, n-propyl, n-butyl, n-pentyl, n-hexyl, isopropyl, sec-butyl, tert-butyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl among others.

Useful $C_3$-$C_6$-cycloalkyl groups include cyclopropyl, cyclobutyl, cyclopentyl, cyclohexyl.

Preferably, the $C_1$-$C_7$-acyl moiety of N-acylated dipeptides Acyl-X-Q is an acetyl-group, i.e. preferably $R^4$ is methyl.

According to the present invention the acyl group of N-acylated dipeptides Acyl-X-Q is attached via an amide bond to the amino-terminus of L-amino acid X.

Preferably the set of N-acylated dipeptides Acyl-X-Q in culture media of the present invention is selected from acetyl-A-Q, acetyl-G-Q, acetyl-N-Q or mixtures thereof. Very preferably the set of N-acylated dipeptides Acyl-X-Q in culture media of the present invention contains only acetyl-A-Q.

All L-glutamine containing substances in the culture media of the present invention can be assigned to either one of two disjoint sets of substances:
(i) N-acylated dipeptides Acyl-X-Q, with Acyl and X as defined in the respective embodiment;
(ii) a set of other L-glutamine sources Qsource.

Accordingly, all substances in the set of L-glutamine containing substances contained in the culture media of the present invention that do not meet the definition of N-acylated dipeptides Acyl-X-Q, with Acyl and X as defined in the respective embodiment, constitute the set of other L-glutamine sources Qsource.

According to the present invention molar ratio R=n(Acyl-X-Q)/n(Qsource) is preferably selected from the following ranges: 0,03 to 20; R=0.04 to 15.67; R=0.05 to 10; R=0.05 to 5. In preferred embodiments of the present invention R is selected from the range R=0.04 to 15.67.

The culture medium of the invention can be in liquid form, in form of a gel, e.g. an agar-agar-, carrageen- or gelatine-containing medium, or can be a powder, a granulate, a pellet or in form of a tablet. In a preferred embodiment, the culture medium is in liquid form.

Preferably, the culture medium is in sterile form.

In preferred embodiments, the culture media of the invention are chemically defined media, or serum-free media. In further preferred embodiments, the culture media of the invention are chemically defined media. In order to obtain such media, for example, N-acylated dipeptides Acyl-X-Q may be supplemented to the CHOMACS CD medium of Miltenyl Biotech (Bergisch Gladbach, Germany), to the PowerCHO-2 CD medium available from LONZA (Basel, Switzerland), the Acti-CHO P medium of PAA (PAA Laboratories, Pasching, Austria), the Ex-Cell CD CHO medium available from SAFC, the SFM4CHO medium and the CDM4CHO medium of ThermoFisher (Waltham, USA), DMEM medium (Life Technologies Corp., Carlsbad, USA), thus yielding suitable stoichiometric ratios of sources of L-glutamine, as specified by the invention. The present invention, however, is not limited to supplementation of the above media.

In one embodiment of the invention, the culture medium does not contain a growth factor. In some embodiments of the invention, the culture medium does not contain any lipids.

In other preferred embodiments, the culture media of the invention are liquid media concentrates in 2-fold, 3-fold, 3.33-fold, 4-fold, 5-fold or 10-fold concentrated form (volume/volume), relative to the concentration of said media in use. This allows preparation of "ready-to-use" culture media by simple dilution of the concentrated media with the respective volume of sterile water. Such concentrated forms of the media of the invention may also be used by addition of the same to a culture, e.g., in a fed-batch cultivation process.

Culture media of the present invention preferably contain all nutrients required for sustained growth and product formation. Recipes for preparing culture media, in particular cell culture media, are well known to the person skilled in the art (see, e.g., Cell Culture Technology for Pharmaceutical and Cell-Based Therapies, Öztürk and Wei-Shou Hu eds., Taylor and Francis Group 2006). Various culture media are commercially available from various sources.

The culture media of the invention preferably include a carbohydrate source. The main carbohydrate used in cell culture media is glucose, routinely supplemented at 5 to 25 nM. In addition, any hexose, such as galactose, fructose, or mannose or a combination may be used.

The culture media typically also include at least the essential amino acids (i.e., His, Ile, Leu, Lys, Met, Phe, Thr, Tyr, Val) as well as certain non-essential amino acids. A non-essential amino acid is typically included in the cell culture medium if the cell line is not capable of synthesizing the amino acid or if the cell line cannot produce sufficient quantities of the amino acid to support maximal growth.

The culture media of the invention preferably comprise salts. Salts are added to cell culture medium to maintain isotonic conditions and prevent osmotic imbalances. The osmolality of a culture medium of the invention is about 300 mOsm/kg, although many cell lines can tolerate an approximately 10 percent variation of this value or higher. The osmolality of some insect cell cultures tend to be higher than 300 mOsm/kg, and this may be 0.5 percent, 1 percent, 2 to 5 percent, 5-10 percent, 10-15 percent, 15-20 percent, 20-25 percent, 25-30 percent higher than 300 mOsm/kg. The most commonly used salts in cell culture medium include $Na^+$, $K^+$, $Mg^{2+}$, $Ca^{2+}$, $Cl^-$, $SO_4^{2-}$, $PO_4^{3-}$, and $HCO_3^-$ (e.g., $CaCl_2$, KCl, NaCl, $NaHCO_3$, $Na_2HPO_4$).

Other inorganic elements may be present in the culture medium. They include Mn, Cu, Zn, Mo, Va, Se, Fe, Ca, Mg, Si, and Ni. Many of these elements are involved in enzymatic activity. They may be provided in the form of salts such as $CaCl_2$, $Fe(NO_3)_3$, $MgCl_2$, MgSO4, $MnCl_2$, NaCl, $NaHCO_3$, $Na_2HPO_4$, and ions of the trace elements, such as, selenium, vanadium and zinc. These inorganic salts and trace elements may be obtained commercially, for example from Sigma (Saint Louis, Mo.).

The culture media of the invention preferably comprise vitamins. Vitamins are typically used by cells as cofactors. The vitamin requirements of each cell line vary greatly, although generally extra vitamins are needed if the cell culture medium contains little or no serum or if the cells are grown at high density. Exemplary vitamins preferably present in culture media of the invention include biotin, choline chloride, folic acid, i-inositol, nicotinamide, D-Ca++-pantothenate, pyridoxal, riboflavin, thiamine, pyridoxine, niacinamide, A, B6, B12, C, D3, E, K, and p-aminobenzoic acid (PABA).

Complex culture media according to the invention may also comprise serum. Serum is the supernatant of clotted blood. Serum components include attachment factors, micronutrients (e.g., trace elements), growth factors (e.g., hormones, proteases), and protective elements (e.g., antitoxins, antioxidants, antiproteases). Serum is available from a variety of animal sources including human, bovine or equine serum. When included in cell culture medium according to the invention, serum is typically added at a concentration of 5-10% (vol.). Preferred cell culture media are serum-free.

To promote cell growth in the absence of serum or in serum reduced media, one or more of the following polypeptides can be added to a cell culture medium of the invention: for example, fibroblast growth factor (FGF), including acidic FGF and basic FGF, insulin, insulin-like growth factor (IGF), epithelial growth factor (EGF), nerve growth factor (NGF), platelet-derived growth factor (PDGF), and transforming growth factor (TGF), including TGFalpha and TGFbeta, any cytokine, such as interleukins 1, 2, 6, granulocyte stimulating factor, leukocyte inhibitory factor (LIF), etc. However, the culture medium of the invention may also include none of the above listed growth factors.

In other embodiments, the cell culture medium does not comprise polypeptides (i.e., peptides with more than 20 amino acids).

One or more lipids can also be added to a cell culture medium of the invention, such as linoleic acid, linolenic acid, arachidonic acid, palmitoleic acid, oleic acid, polyenoic acid, and/or fatty acids of 12, 14, 16, 18, 20, or 24 carbon atoms, each carbon atom branched or unbranched), phospholipids, lecithin (phophatidylcholine), and cholesterol. One or more of these lipids can be included as supplements in serum-free media. Phosphatidic acid and lysophosphatidic acid stimulate the growth of certain anchorage-dependent cells, such as MDCK, mouse epithelial, and other kidney cell lines, while phosphatidylcholine, phosphatidylethanolamine, and phosphatidylinositol stimulate the growth of human fibroblasts in serum-free media. Ethanolamine and cholesterol have also been shown to promote the growth of certain cell lines. In certain embodiment, the cell culture medium does not contain a lipid.

One or more carrier proteins, such as bovine serum albumin (BSA) or transferrin, can also be added to the cell culture medium. Carrier proteins can help in the transport of certain nutrients or trace elements. BSA is typically used as a carrier of lipids, such as linoleic and oleic acids, which are insoluble in aqueous solution. In addition, BSA can also serve as a carrier for certain metals, such as Fe, Cu, and Ni. In protein-free formulations, non-animal derived substitutes for BSA, such as cyclodextrin, can be used as lipid carriers.

One or more attachment proteins, such as fibronectin, laminin, and pronectin, can also be added to a cell culture medium to help promote the attachment of anchorage-dependent cells to a substrate.

The cell culture medium can optionally include one or more buffering agents. Suitable buffering agents include, but are not limited to, N-[2-hydroxyethyl]-piperazine-N'-[2-ethanesulfonic acid] (HEPES), MOPS, MES, phosphate, bicarbonate and other buffering agents suitable for use in cell culture applications. A suitable buffering agent is one that provides buffering capacity without substantial cytotoxicity to the cells cultured. The selection of suitable buffering agents is within the ambit of ordinary skill in the art of cell culture.

Polyanionic or polycationic compounds may be added to the culture medium to prevent the cells from clumping and to promote growth of the cells in suspension.

In preferred embodiments, the total concentration of N-acylated dipeptides Acyl-X-Q present in liquid culture media according to the invention is in the range of from 0.01 g/l to 20 g/l, or 0.1 g/l to 10 g/l, or 0.5 g/l to 5 g/l. In other preferred embodiments, the total concentration of N-acylated dipeptides Acyl-X-Q present in liquid culture media according to the invention is above 0.01 mM, 0.02 mM, 0.04 mM, 0.08 mM, 0.2 mM, 0.4 mM, or 1 mM. Also preferred are liquid culture media wherein the total concentration of N-acylated dipeptides Acyl-X-Q present is less than 50 mM, 20 mM, 10 mM, 5 mM, or 2 mM. Preferably, the total concentration of N-acylated dipeptides Acyl-X-Q present in liquid culture media according to the invention is in the range of from 0.01 mM to 40 mM, or 0.1 mM to 20 mM, or 0.1 mM to 10 mM, or 0.5 mM to 10 mM, or 1 mM to 10 mM, or 1 mM to 8 mM, or 1 mM to 6 mM. In a very preferred embodiment, the total concentration of N-acylated dipeptides Acyl-X-Q present in liquid culture media according to the invention is from 1 mM to 8 mM, Acyl is as an acetyl group, and X is Alanine. The above concentrations are given as concentrations in the non-concentrated medium, i.e., the concentration as present in the actual culture. Concentrated media may include X-fold higher concentrations.

The culture medium of the present invention can be in concentrated form. It may be, e.g., in 2-fold, 3-fold, 3.33-fold, 4-fold, 5-fold, 10-fold, 20-fold, 50-fold or 100-fold concentrated form (relative to a concentration that supports growth and product formation of the cells). Such concentrated culture media are helpful for preparing the culture medium for use by dilution of the concentrated culture medium with an aqueous solvent, such as water. Such concentrated culture media may be used in batch culture, but are also advantageously used in fed-batch or continuous cultures, in which a concentrated nutrient composition is added to an ongoing cultivation of cells, e.g., to replenish nutrients consumed by the cells during culture.

The present invention also relates to the use of a culture medium of the invention for culturing cells.

Another aspect of the invention relates to the use of a culture medium of the invention for producing a cell culture product.

A preferred embodiment of the invention relates to the use of a culture medium according to the invention for culturing animal cells or plant cells, most preferred mammalian cells. In specific embodiments the cells to be cultured are CHO cells, COS cells, VERO cells, BHK cells, HEK cells, HELA cells, AE-1 cells, insect cells, fibroblast cells, muscle cells, nerve cells, stem cells, skin cells, endothelial cells and hybridoma cells. Preferred cells of the invention are CHO cells and hybridoma cells. Most preferred cells of the invention are CHO cells. Particularly preferred CHO cells of the invention are CHO DG44 and CHO DP12 cells.

Also included in the scope of the present invention is a method of culturing cells, said method comprising contacting said cells with a cell culture medium according to the invention. In one embodiment of the invention, the method of culturing cells comprises contacting the cell with a basal culture medium under conditions supporting the cultivation of the cell and supplementing the basal cell culture medium with a concentrated medium according to the present invention. In preferred embodiments, the basal culture medium is supplemented with the concentrated feed or medium on more than one day.

Another aspect of the invention relates to a method of producing a culture medium according to the invention. Methods of producing a culture medium according to the invention comprise at least one step of adding at least one N-acylated dipeptide Acyl-X-Q of the invention to the culture medium. Likewise, an aspect of the invention relates to the use of at least one N-acylated dipeptide Acyl-X-Q of the invention for producing a cell culture medium.

Another aspect of the invention relates to a method of modifying a culture medium, wherein said modifying of said culture medium comprises addition of at least one N-acylated dipeptide Acyl-X-Q of the invention to said culture medium.

Another aspect of the invention relates to a method of producing a liquid culture medium, said method comprising providing solid medium according to the invention, e.g., in form of a dry powder, or in form of granules, or in form of pellets, or in form of tablets; and dissolving said solid culture medium in an aqueous medium, such as water.

Another aspect of the invention relates to the use of at least one N-acylated dipeptide Acyl-X-Q according to the invention for culturing cells. Another aspect of the invention relates to the use of at least one N-acylated dipeptide Acyl-X-Q according to the invention for cell culture.

The invention also relates to methods of manufacturing a cell culture product comprising the steps of (i) providing a cell capable of producing said cell culture product; (ii) contacting said cell with a culture medium of the invention; and (iii) obtaining said cell culture product from said culture medium or from said cell. Likewise, the present invention relates to the use of at least one N-acylated dipeptide Acyl-X-Q according to the invention for manufacturing a cell culture product.

In preferred methods, the cell culture product is a therapeutic protein, a diagnostic protein, a polysaccharide, such as heparin, an antibody, a monoclonal antibody, a growth factor, an interleukin, virus, virus-like particle or an enzyme.

Cultivation of cells, according to the invention can be performed in batch culture, in fed-batch culture or in continuous culture.

In a preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 1 to 8 mM, and the cell is a CHO cell. In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 1 to 8 mM, and the cell is a CHO cell or a hybridoma cell. In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 1 to 8 mM, and the cell is a mammalian cell. In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 0.5 to 10 mM, and the cell is a CHO cell. In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 0.5 to 10 mM, and the cell is a CHO cell or a hybridoma cell. In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 0.5 to 10 mM, and the cell is a mammalian cell.

In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 0.1 to 20 mM, and the cell is a CHO cell. In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 0.1 to 20 mM, and the cell is a CHO cell or a hybridoma cell. In another preferred method of cultivating cells, or use of at least one N-acylated dipeptide Acyl-X-Q for the cultivation of cells, according to the invention, the N-acylated dipeptide Acyl-X-Q is Acetyl-A-Q, Acetyl-A-Q is present at a concentration of from 0.1 to 20 mM, and the cell is a mammalian cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 1 to 8 mM, and the cell is a CHO cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 1 to 8 mM, and the cell is a CHO cell or a hybridoma cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 1 to 8 mM, and the cell is a mammalian cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 0.5 to 10 mM, and the cell is a CHO cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 0.5 to 10 mM, and the cell is a CHO cell or a hybridoma cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 0.5 to 10 mM, and the cell is a mammalian cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 0.1 to 20 mM, and the cell is a CHO cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 0.1 to 20 mM, and the cell is a CHO cell or a hybridoma cell. In another preferred method of cultivating cells, or use of at least one N-acylated dipeptide Acyl-X-Q for the cultivation of cells, according to the invention, the N-acylated dipeptide Acyl-X-Q is Acyl-A-Q, Acyl-A-Q is present at a concentration of from 0.1 to 20 mM, and the cell is a mammalian cell.

In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 1 to 8 mM, and the cell is a CHO cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 1 to 8 mM, and the cell is a CHO cell or a hybridoma cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 1 to 8 mM, and the cell is a mammalian cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 0.5 to 10 mM, and the cell is a CHO cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 0.5 to 10 mM, and the cell is a CHO cell or a hybridoma cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 0.5 to 10 mM, and the cell is a mammalian cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 0.1 to 20 mM, and the cell is a CHO cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 0.1 to 20 mM, and the cell is a CHO cell or a hybridoma cell. In another preferred method of cultivating cells, or use of at least one N-acylated dipeptide Acyl-X-Q for the cultivation of cells, according to the invention, N-acylated dipeptides Acyl-X-Q are selected from Acyl-A-Q, Acyl-G-Q or mixtures thereof, with N-acylated dipeptides Acyl-X-Q present at a total concentration of from 0.1 to 20 mM, and the cell is a mammalian cell.

In preferred embodiments of the present invention the set of N-acylated dipeptides Acyl-X-Q, the set of other L-glutamine sources Qsource and the molar ratio $R = n(Acyl-X-Q)/n(Qsource)$ are defined as listed below; in such preferred embodiments the cell culture media are chemically defined media and N-acylated dipeptides Acyl-X-Q are present at a total concentration of from 1 mM to 8 mM; in preferred uses of and processes for the manufacture of cell culture products, CHO cells are contacted with such preferred cell culture media:

|   | Acyl-X-Q | Qsource | R |
|---|---|---|---|
| 1 | one or more of acetyl-A-Q, acetyl-G-Q, acetyl-N-Q | free Q and/or A-Q | 0.03 to 20 |
| 2 | one or more of acetyl-A-Q, acetyl-G-Q, acetyl-N-Q | free Q and/or A-Q | 0.04 to 15.67 |
| 3 | one or more of acetyl-A-Q, acetyl-G-Q, acetyl-N-Q | free Q and/or A-Q | 0.05 to 10 |
| 4 | one or more of acetyl-A-Q, acetyl-G-Q, acetyl-N-Q | free Q | 0.03 to 20 |
| 5 | one or more of acetyl-A-Q, acetyl-G-Q, acetyl-N-Q | free Q | 0.04 to 15.67 |
| 6 | one or more of acetyl-A-Q, acetyl-G-Q, acetyl-N-Q | free Q | 0.05 to 10 |

-continued

| | Acyl-X-Q | Qsource | R |
|---|---|---|---|
| 7 | one or more of acetyl-A-Q, acetyl-G-Q, acetyl-N-Q | A-Q | 0.03 to 20 |
| 8 | one or more of acetyl-A-Q, acetyl-G-Q, acetyl-N-Q | A-Q | 0.04 to 15.67 |
| 9 | one or more of acetyl-A-Q, acetyl-G-Q, acetyl-N-Q | A-Q | 0.05 to 10 |
| 10 | acetyl-A-Q | free Q and/or A-Q | 0.03 to 20 |
| 11 | acetyl-A-Q | free Q and/or A-Q | 0.04 to 15.67 |
| 12 | acetyl-A-Q | free Q and/or A-Q | 0.05 to 10 |
| 13 | acetyl-A-Q | free Q | 0.03 to 20 |
| 14 | acetyl-A-Q | free Q | 0.04 to 15.67 |
| 15 | acetyl-A-Q | free Q | 0.05 to 10 |
| 16 | acetyl-A-Q | A-Q | 0.03 to 20 |
| 17 | acetyl-A-Q | A-Q | 0.04 to 15.67 |
| 18 | acetyl-A-Q | A-Q | 0.05 to 10 |
| 19 | acetyl-G-Q | free Q and/or A-Q | 0.03 to 20 |
| 20 | acetyl-G-Q | free Q and/or A-Q | 0.04 to 15.67 |
| 21 | acetyl-G-Q | free Q and/or A-Q | 0.05 to 10 |
| 22 | acetyl-G-Q | free Q | 0.03 to 20 |
| 23 | acetyl-G-Q | free Q | 0.04 to 15.67 |
| 24 | acetyl-G-Q | free Q | 0.05 to 10 |
| 25 | acetyl-G-Q | A-Q | 0.03 to 20 |
| 26 | acetyl-G-Q | A-Q | 0.04 to 15.67 |
| 27 | acetyl-G-Q | A-Q | 0.05 to 10 |
| 28 | acetyl-N-Q | free Q and/or A-Q | 0.03 to 20 |
| 29 | acetyl-N-Q | free Q and/or A-Q | 0.04 to 15.67 |
| 30 | acetyl-N-Q | free Q and/or A-Q | 0.05 to 10 |
| 31 | acetyl-N-Q | free Q | 0.03 to 20 |
| 32 | acetyl-N-Q | free Q | 0.04 to 15.67 |
| 33 | acetyl-N-Q | free Q | 0.05 to 10 |
| 34 | acetyl-N-Q | A-Q | 0.03 to 20 |
| 35 | acetyl-N-Q | A-Q | 0.04 to 15.67 |
| 36 | acetyl-N-Q | A-Q | 0.05 to 10 |

EXAMPLES

Example 1

Mixture of Acetyl-A-Q with Different Glutamine Sources in Batch Cultivation

Acetyl-A-Q was mixed with free glutamine or A-Q in molar ratios between 0 and 100%. The mixtures were added to a glutamine-free medium (PowerCHO-2 CD, Lonza AG, Visp, Switzerland) to obtain a total glutamine concentration of 8 mM in the final medium. Growth and productivity were measured using Chinese Hamster Ovary (CHO) cells (Subclone DG44; Life Technologies Cooperation, Carlsbad, USA). Cultivation was continued up to the point where the viability of the culture dropped below 80%. Data from the third passage was used. The results for mixing acetyl-A-Q with free glutamine (Q) are summarized in Table 1. All titer-related information is given relative to the titer of 100% free glutamine. Accordingly, the relative cell-specific productivity was obtained by first dividing the relative titer by the integrated viable cell density (IVCD), then dividing this number by the titer/IVCD ratio for 100% free glutamine. The relative time-specific productivity was obtained by dividing the relative titer by the cultivation duration until the sampling, then dividing this number by the titer/cultivation time ratio for free glutamine.

TABLE 1

| | 100% acetyl-A-Q | 75% acetyl-A-Q, 25% Q | 50% acetyl-A-Q, 50% Q | 25% acetyl-A-Q, 75% Q | 100% Q, reference |
|---|---|---|---|---|---|
| Integrated viable cell density (IVCD) | 10.1 | 41.3 | 42.7 | 32.2 | 32.0 |
| Cultivation time until 80% viability | 17.9 | 12.9 | 13.9 | 11.9 | 12.9 |
| Relative titer | 1.37 | 1.16 | 1.10 | 1.10 | 1.00 |
| Relative cell-specific productivity | 434% | 89% | 82% | 109% | 100% |
| Relative time-related productivity | 99% | 116% | 102% | 119% | 100% |

Using 100% acetyl-A-Q yields the best values for relative titer and cell-specific productivity, but the sub-critical cell density can make the culture less robust. Surprisingly, adding free glutamine increases the relative time-related productivity. The best combination of relative titer and time-related productivity was found with 75% acetyl-A-Q and 25% free glutamine.

In a second set of experiments within the same experimental campaign, acetyl-A-Q was mixed with A-Q and tested under the same conditions as described above. The 100% points for acetyl-A-Q as well as the free glutamine reference are identical to the first example.

TABLE 2

| | 100% acetyl-A-Q | 75% acetyl-A-Q, 25% AQ | 50% acetyl-A-Q, 50% AQ | 25% acetyl-A-Q, 75% AQ | 100% AQ | 100% Q, reference |
|---|---|---|---|---|---|---|
| Integrated viable cell density (IVCD) | 10.1 | 31.8 | 38.7 | 38.7 | 47.1 | 32.0 |
| Cultivation time until 80% viability | 17.9 | 13.9 | 12.9 | 12.9 | 13.9 | 12.9 |
| Relative titer | 1.37 | 1.46 | 1.25 | 1.12 | 1.10 | 1.00 |
| Relative cell-specific productivity | 434% | 147% | 103% | 93% | 75% | 100% |

TABLE 2-continued

|  | 100% acetyl-A-Q | 75% acetyl-A-Q, 25% AQ | 50% acetyl-A-Q, 50% AQ | 25% acetyl-A-Q, 75% AQ | 100% AQ | 100% Q, reference |
|---|---|---|---|---|---|---|
| Relative time-related productivity | 99% | 136% | 125% | 112% | 102% | 100% |

Surprisingly, the supplement made by combining 75% acetyl-A-Q with 25% A-Q led to the best combination of cell-specific and time-specific productivities as well as relative titer. It is also superior to the combination of acetyl-A-Q and free glutamine. The current industry standard, a supplementation with 100% A-Q, performs at a lower level in all relevant categories.

Example 2

Mixture of Acetyl-A-Q with Different Glutamine Sources in Fed-Batch Cultivation

Free glutamine, A-Q or Acetyl-A-Q were added to a glutamine-free medium (PowerCHO-2 CD, Lonza AG, Visp, Switzerland) to obtain a total glutamine concentration of 8 mM in the final medium.

In addition, these substances as well as a 75% mixture of acetyl-A-Q and A-Q were added to a glutamine-free formulation of a commercial feed supplement (CHOMACS Feed Supplement, Miltenyi Biotech, Germany) to yield a glutamine concentration of 5.5 g/L. Growth and productivity were measured using Chinese Hamster Ovary (CHO) cells (Subclone DG44; Life Technologies Cooperation, Carlsbad, USA). The results are summarized in Table 3. All titer-related information is given relative to the titer obtained by adding free glutamine to basal medium and feed. Accordingly, the relative cell-specific productivity was obtained by first dividing the relative titer by the integrated viable cell density (IVCD), then dividing this number by the titer/IVCD ratio for 100% free glutamine. The relative time-specific productivity was obtained by dividing the relative titer by the cultivation duration until the sampling, then dividing this number by the titer/cultivation time ratio for free glutamine.

Surprisingly, the same tendencies were found for a fed-batch operation. Cultivating only with acetyl-A-Q led to very high cell-specific productivities, but very low cell density. In this specific set of experiments, it even led to very low titer levels. These experiments also showed that the previously selected combination of acetyl-A-Q and A-Q in a 75%/25% ratio can also successfully be used as glutamine source for a feed supplement. In summary, combining a glutamine source such as Q or A-Q in the basal medium with acetyl-A-Q in the feed always performed better than a combination of Q or A-Q in the feed. Combining A-Q in the basal medium with a mixture of acetyl-A-Q and A-Q in the feed led to the best performance combination overall.

The invention claimed is:
1. A cell culture media, comprising
   L-glutamine from a set of N-acylated dipeptides Acyl-XQ; and
   L-glutamine from a set of other glutamine-sources Qsource in a defined molar ratio R=n(Acyl-X-Q)/n(Qsource),
   wherein:
   X is defined as an L-amino acid;
   Q is defined as L-glutamine attached via an amide bond to L-amino acid X;
   Acyl is defined as a C1-C7-acyl moiety attached via an amide bond to the amino-terminus of L-amino acid X;
   R is defined to be in the range of 0.03 to 20;
   n(Acyl-X-Q) is the total amount of substance of L-glutamine contained in the set of N-acylated dipeptides Acyl-X-Q in the culture media;
   n(Qsource) is the total amount of substance of L-glutamine contained in the set of other glutamine sources Qsource in the culture media;

TABLE 3

|  | Q/Q | Q/A-Q | Q/acetyl-A-Q | A-Q/A-Q | A-Q/acetyl-A-Q | A-Q/6:2 mixture of acetyl-A-Q and A-Q | Acetyl A-Q/acetyl-A-Q |
|---|---|---|---|---|---|---|---|
| Integrated viable cell density (IVCD) | 61.0 | 63.0 | 59.5 | 54.4 | 46.3 | 51.8 | 8.2 |
| Cultivation time until 80% viability | 14.0 | 14.0 | 15.0 | 17.0 | 17.0 | 17.0 | 15.0 |
| Relative titer | 1.0 | 1.1 | 1.2 | 1.1 | 1.2 | 1.2 | 0.2 |
| Relative cell-specific productivity | 100% | 107% | 126% | 129% | 153% | 141% | 145% |
| Relative time-related productivity | 100% | 111% | 115% | 95% | 96% | 99% | 18% | the constituents of the set of other L-glutamine sources Qsource are selected from the following: Free L-glutamine, dipeptides Y-Q, or mixtures thereof, wherein Y is defined as one of the 20 genetically encoded L-amino acids, wherein Q is defined as L-glutamine attached via an amide bond to L-amino acid Y, and the amide bond connecting Y and Q in dipeptide Y-Q is a regular backbone amide bond involving the carboxy terminus of amino acid Y and the amino terminus of glutamine Q; and the cell culture media are serum free.

2. The cell culture media according to claim 1, wherein the cell culture media are chemically defined.

3. The cell culture media according to claim 1, wherein the only constituent of the set of other L-glutamine sources Qsource is dipeptide Y-Q, wherein Y is Alanine.

4. The cell culture media according to claim 1, wherein the only constituent of the set of other L-glutamine sources Qsource is free L-glutamine.

5. The cell culture media according to claim 1, wherein the total concentration of N-acylated dipeptides Acyl-X-Q is in the range of from 1 mM to 8 mM.

6. The cell culture media according to claim 1, wherein the molar ratio R=n(Acyl-X-Q)/n(Qsource) is defined to be in the range of 0.04 to 15.67.

7. The cell culture media according to claim 1, wherein the set of N-acylated dipeptides Acyl-X-Q is defined as follows: One or more of acetyl-A-Q, acetyl-G-Q, acetyl-NQ.

8. The cell culture media according to claim 1, wherein the set of N-acylated dipeptides Acyl-X-Q is defined as follows: One or more of acetyl-A-Q, acetyl-G-Q.

9. The cell culture media according to claim 1, wherein the set of N-acylated dipeptides Acyl-X-Q is defined as follows: Acetyl-A-Q.

10. The cell culture media according to claim 1, wherein:
the cell culture media are chemically defined;
the only constituent of the set of other L-glutamine sources Qsource is dipeptide Y-Q, wherein Y is Alanine;
the molar ratio R=n(Acyl-X-Q)/n(Qsource) is defined to be in the range of 0.04 to 15.67;
the set of N-acylated dipeptides Acyl-X-Q is defined as follows: Acetyl-A-Q; and
the concentration of acetyl-A-Q is in the range of from 1 mM to 8 mM.

11. A process, comprising culturing cells with the cell culture media of claim 1.

12. A process for manufacturing a cell culture product, the process comprising contacting cells with the cell culture medium of claim 1.

13. The process according to claim 12, wherein the cells contacted with the cell culture medium are Chinese hamster ovary (CHO) cells.

* * * * *